United States Patent [19]
Hildebrandt et al.

[11] Patent Number: 4,851,218
[45] Date of Patent: Jul. 25, 1989

[54] METHOD FOR CONTROLLING INSECTS OF THE FAMILY VESPIDAE UTILIZING INTERSPECIFIC INSECTICIDAL BAIT

[75] Inventors: Donald W. Hildebrandt; Richard E. Keyel, both of Racine, Wis.

[73] Assignee: S. C. Johnson & Son, Inc., Racine, Wis.

[21] Appl. No.: 920,321

[22] Filed: Oct. 16, 1986

Related U.S. Application Data

[63] Continuation of Ser. No. 729,337, May 1, 1985, abandoned.

[51] Int. Cl.$^4$ ............................................. A01N 25/00
[52] U.S. Cl. ...................................................... 424/84
[58] Field of Search ........................................... 424/84

[56] References Cited

U.S. PATENT DOCUMENTS

| 3,485,868 | 12/1969 | Eddy et al. | 424/84 |
| 3,717,706 | 2/1973 | McGovern et al. | 424/84 |
| 3,790,666 | 2/1974 | Eddy et al. | 424/84 |
| 3,798,318 | 3/1974 | Wright | 424/84 |
| 3,912,810 | 10/1975 | Eddy et al. | 424/84 |
| 3,932,616 | 1/1976 | Meresz et al. | 424/84 |
| 4,016,220 | 4/1977 | Küpper et al. | 424/84 |
| 4,122,165 | 10/1978 | Kinzer et al. | 424/84 |
| 4,205,066 | 5/1980 | Hennart et al. | 424/84 |

FOREIGN PATENT DOCUMENTS 7811632  5/1980  Netherlands ........................... 424/84

OTHER PUBLICATIONS

*Advances in Pest Control Research* Metcalf (ed.) vol. 8, 1968, p. 88.

Primary Examiner—Douglas W. Robinson

[57] ABSTRACT

A method for control of insects from the family Vespidae is disclosed. It has been discovered that (Z)-9-tricosene, (Z)-9-heneicosene and the saturated hydrocarbons tricosane and tridecane act as kairomones for the family Vespidae to locate its prey, the house fly. By incorporating these materials as attractants in a proteinaceous matrix having a delayed toxicant, control over colonies of Vespidae may be achieved.

5 Claims, 1 Drawing Sheet

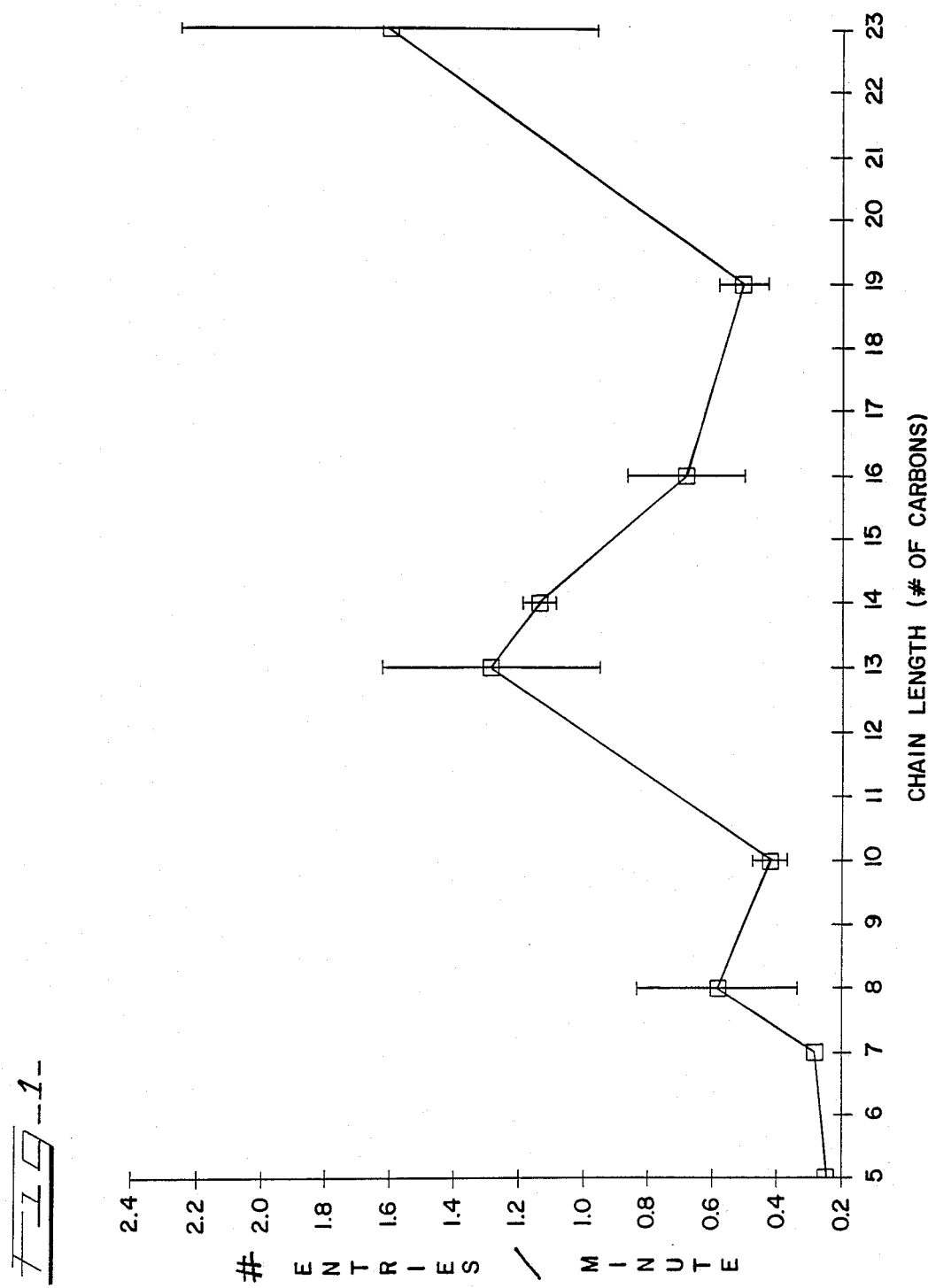

METHOD FOR CONTROLLING INSECTS OF THE FAMILY VESPIDAE UTILIZING INTERSPECIFIC INSECTICIDAL BAIT

REFERENCE TO RELATED APPLICATION

This application is a continuation of patent application Ser. No. 729,337, filed May 1, 1985, now abandoned, the benefit of which is now claimed for purposes of priority pursuant to 35 USC §120.

FIELD OF THE INVENTION

This invention relates to compositions useful in attracting insects of the family Vespidae and most particularly yellowjacket wasps, to a bait containing a toxicant which may have delayed toxicity and which is adapted to be carried back to the nest of the yellow jacket wasps for contamination and eradication of the nest itself. The primary attractive compounds in the attractive insecticidal bait of the present invention are synthesized and natural versions of a naturally occurring long chain hydrocarbon known as (Z)-9-tricosene and related compounds such as (Z)-9-heneicosene and tricosane. The naturally occurring long chain hydrocarbons are both saturated and unsaturated aliphatic compounds having a carbon content of $C_5$ to $C_{33}$ and particularly $C_8$ to $C_{23}$. These compounds are semiochemicals which are the sex pheromones of the common house fly *Musca domestica* which serve as allelochemics and specifically serve as kairomones for the predatory yellowjacket wasps. This discovery of incorporating (Z)-9-tricosene and its homologs into a system containing a toxic base bait offers a new means for controlling yellowjacket wasps in areas where their presence is considered to be a nuisance.

Semiochemicals are naturally occurring chemicals given off by insects and other arthropods which serve as chemical communicants. Semiochemicals are divided into two broad groups, pheromones and allelochemics, depending on whether the interactions are intraspecific or interspecific, respectively. It is not unknown for a semiochemical to serve as a pheromone as between members of the same species and allelochemic as between members of different species. It has been discovered in the present invention that the chemical pheromones (Z)-9-tricosene and (Z)-9-heneicosene, as well as tricosane, tridecane and other long chain hydrocarbons, both saturated and unsaturated having a carbon content of $C_5$ to $C_{33}$, and particularly $C_8$ to $C_{23}$, will serve as an attractant for the yellowjackets of the family Vespidae, and more particularly for *Vespula flavopilosa, Vespula germanica, Vespula maculifrons, Vespula squamosa, Vespula vulgaris* and *Vespula pensylvanica*. Thus, it may be seen that (Z)-9-tricosene, (Z)-9-heneicosene and tricosane act as allelochemics and more particularly as kairomones for the yellowjacket wasp to allow the yellowjacket to locate its intended prey, namely the house fly.

Kinzer et al U.S. Pat. No. 4,122,165 relates to an insecticidal composition for the control of Diptera such as *Musca domestica*, comprising a (cis)-9-tricosene as the attractant and methomyl as the toxicant with a carrier substance. It is taught by Kinzer that by the use of the sex pheromone (cis)-9-tricosene, Diptera are attracted to the methomyl toxicant and eradicated or at least controlled.

Kinzer differs from the present invention in that Kinzer utilizes the well known theory of use of a pheromone in its classical definition; namely, as an attractant which is intraspecific with a given species. Kinzer does not recognize nor does he teach the use of the naturally occurring pheromone (cis)-9-tricosene as an allelochemic and more specifically as a kairomone whereby an interspecific response is elicited as between different species of insects. Moreover, Kinzer does not recognize that a variety of chemicals may be used to elicit a response from both the common house fly and its predator, the yellowjacket wasp. In addition, Kinzer does not recognize the action of (Z)-9-heneicosene, tricosane, tridecane and mixtures thereof as well as a number of other saturated and unsaturated aliphatic hydrocarbons having a carbon content of $C_5$ to $C_{33}$ and more particularly $C_8$ to $C_{23}$ as allelochemics for the control of insect pests.

The present invention is concerned with the use of the pheromones (Z)-9-tricosene as well as tricosane, tridecane (Z)-9-heneicosene and mixtures thereof for use as a kairomone for a cross species attraction between the yellowjacket wasp and the trap or attractant toxicant. It is obvious to those skilled in the art that IUPAC has adopted new nomenclature and that cis is now identified by Zusammen (Z) and trans is identified by entgagen (E). The toxicant may be in a powdered form or incorporated into a bait whereby the insect becomes attracted to the toxicant and becomes infected with the toxicant or carries the toxicant back to the nest where it is spread throughout the nest and eradicates the members of the colony. In the alternative, it may be seen that by coating traps with (Z)-9-tricosene, or other attractants, good control may be had over yellowjackets in the area.

SUMMARY OF THE INVENTION

This invention consists of a suitable matrix which is acceptable for ingestion by wasps, or for transfer to a wasp nest by foraging members of the colony. Attractant compounds include, but are not to be limited to, (Z)-9-tricosene, Z-(9)-heneicosene, tricosane, and tridecanes. It should be noted that it has been determined that saturated and unsaturated aliphatic compounds having a carbon content of $C_5$ to $C_{33}$ and particularly $C_8$ to $C_{23}$ have proven useful in attracting yellowjacket wasps to traps. Thus, although the four chemicals specifically named are preferred, they are not in any way to be construed as limiting as to the compounds which are useful in the present invention. Moreover, it is not critical as to the amount of attractant present. Rather the attractant may be used in any amount sufficient to attract pestiferous wasps.

Toxicants which may be useful in this invention are those which will not adversely affect the attractiveness of the bait and neither will they interact with the (Z)-9-tricosene or (Z)-9-heneicosene or tricosane or tridecane, and mixtures thereof, such that the wasps are unable to detect its presence thereby insuring the effectiveness of the toxicant and attractant combination. A variety of matrix materials may also be employed as a carrier for the toxicant.

The invention may also include a bait matrix which is conducive to being transported back to the nest by the foraging insects. In addition to the toxic ingestion of amounts of this attractant bait, the use of additional toxic material in the form of dust or powder together with the attractant described will serve to increase the total killing power of the formulation, especially as the insect touches the bait with parts of its body or appendages in addition to its mouth parts. It would be expected that such dust or powder as well as material ingested by foragers would be transported back to the nest where killing of the nest dwellers would occur as the infected insect undertakes social conduct within the colony. Further, it must be assumed that the toxicant should necessarily have some delayed toxicity to allow its transport back to the nest by the foraging members of the colony. Thus, instantaneous death of the foragers at the actual trap itself is not the most desirable method in which to eradicate the nest.

Finally, it is conceivable that the attractant may be placed within a trap which allows the insects to enter but prevents their exit. In this manner, the foraging power of the colony is reduced thereby achieving some degree of control over the colony.

It is an object of the present invention to control the population of insects of the family Vespidae in a given area by use of semiochemicals which are allelochemic kairomones for these particular insects.

It is another object of this invention to provide an attractant on a carrier matrix base which attracts the insects of the family Vespidae to the matrix base which is of proteinaceous material acceptable to the insects and impregnated with a toxicant to destroy the foraging members of the colony.

It is another object of the invention to provide an attractant on a carrier base impregnated with a toxicant having delayed toxicity such that the foraging members of the colony become infected with poison and transport the poison back to the colony, thereby infecting and eradicating the entire colony.

Other objects of the invention will become apparent to those skilled in the art by reading the specification.

BRIEF DESCRIPTION OF THE DRAWINGS

FIG. 1 is a graph depicting the number of yellowjackets attracted to bottles containing saturated hydrocarbons of varying chain length.

DETAILED DESCRIPTION OF THE PREFERRED EMBODIMENT

This invention is directed to a highly effective attractant insecticidal composition for insects of the family Vespidae and particularly *Vespula germanica, Vespula pensylvanica, Vespula squamosa, Vespula flavopilosa,* and *Vespula maculifrons, Vespula vulgaris.*

More particularly, this invention relates to a novel composition comprising (Z)-9-tricosene, or (Z)-9-heneicosene tricosane or tridecane, either alone or in combination, and a toxicant having delayed toxicity on a matrix carrier base adaptable to be carried by the foraging members of the wasp colony back to the nest for infection of the entire colony with the toxicant. The composition is preferably (Z)-9-tricosene as the attractant in combination with a proteinaceous material which carries a toxicant having delayed toxicity and preferably an insect growth regulator (IGR). It has been found that the (cis)-9-tricosene acts as an allelochemic kairomone for the yellowjacket wasps and attracts them to the proteinaceous carrier bait material which is laced with any toxicant having a delayed toxicity such as methoprene insect growth regulator, amdro, encapsulated diazinon, organophosphorus compounds or any other toxicant for Hymenoptera having delayed toxicity.

Although the art shows that (cis)-9-tricosene is a sex pheromone of *Musca domestica* and has been used in combination with insecticides for the control of dipteran insects, the effectiveness of the present composition for control of insects of the family Vespidae and particularly *Vespula flavopilosa, Vespula vulgaris, Vespula germanica, Vespula squamosa* and *Vespula maculifrons* is unexpected and could not have been predicted from the prior art.

The attractive pheromone which is to act as a kairomone is a saturated or unsaturated hydrocarbon selected from those having a carbon length of from about $C_5$ to about $C_{33}$ and more particularly from about $C_8$ to about $C_{23}$. The attractant may be extracted from the cutaneous material of the common house fly or from the feces of the house fly. The pheromone is extracted from the cutaneous material or the feces of the animal by suspending the finely ground materials in a liquid and filtering the material through filter chromography whereby the various constituents of the cutaneous material filter to different places in the filter paper. The suitable pheromone or other saturated or unsaturated aliphatic hydrocarbon compounds may then be separated and removed from the filter paper by conventional distillation process by suspension of the filter paper in a suitable solvent such as hexane, heptane, pentane and the like, to leach the compound from the filter paper and then by evaporation of the solvent to leave the compounds desired.

More preferably, a solvent as described above may be applied to the cuticle of the insect to dissolve the desired hydrocarbons into solution. The solvent is then evaporated, leaving the precipitate which is subjected to gas chromatograph readout analysis to isolate and separate the desired hydrocarbons for use in the present invention. The attractant (Z)-9-tricosene is commercially available from Zoecon under the tradename "MUSCAMONE" and all the hydrocarbons within the range specified are commercially available from the Aldrich Company. The compounds may be mixed together or used separately and are preferably placed within a preferably proteinaceous matrix bait compound which is suitable to be carried back to the nest.

The matrix bait is preferably impregnated with a toxicant such as an organophosphorus or other toxicant exhibiting delayed toxicity so that the foraging members of the colony are attracted to the poisoned bait and carry it back with them to the nest where it is fed to the other members of colony, thereby controlling or eradicating the entire colony. It is further contemplated that a suitable amount of the attractant kairomone may be used in conjunction with a powdered pesticide exhibiting delayed toxicity such that the foraging members of the colony are attracted to the trap, where they come in contact with the powdered pesticide. They then travel back to the nest, where they carry the powdered toxicant back with them along their feet and undersides which have contacted the pesticide, to contaminate the nest. Upon grooming themselves or other members of the community, the toxicant is spread thereby eradicating or controlling the colony. The toxicants are selected from the group consisting of organophosphorus toxicants, carbamates, inorganic toxicants, and insect growth regulators.

The organophosphorus compounds are selected from the group consisting of phosphates, phosphorothioates, phosphorothionates and the like. Examples are O-O-Diethyl-O-(3,5,6-trichloro-2-pyridyl) phosphorothionates known under the tradename Chlorpyrifos, O-O-Diethyl-O-(2-isopropyl-6-methyl-5pyrimidinyl) phosphorothioate known under the tradename Diazinon, O-O-Dimethyl-O-(3-methyl-4-nitrophenyl) phosphorothioate known under the tradename Fenitrothion, 2-Diethylamino-6-methylpyrimidin-4-yl dimethyl phosphorothioate known under the tradename Pirimiphos Methyl, O,O-Dimethyl-O-(3-methyl-4-(methylthio)-phenyl) phosphorothioate known under the tradename Fenthion, (Diethoxy-thiophosphoryloxyimino)-phenyl acetonitrile known under the tradename Phoxim, O-S-Dimethyl acetylphosphoramidothioate known under the tradename Acephate, O-2-methylcarbonyl-1-propenyl O-dimethyl phosphorothioate known under the tradename Methacrifos, and the like.

The carbamates may be selected from the group consisting of 2-(1-methylethoxy)phenyl methylcarbamate known under the tradename Propoxur, 2,2-Dimethyl-1,3-benzodioxol-4-yl-N-methyl carbamate known under the tradename Ficam, 2-(1,3-dioxalon-2-yl) phenyl methyl carbamate, known under the tradename Famids, 1-napthyl methylcarbamate known under the tradename Sevin, and the like.

The inorganic toxicants may be selected from the group consisting of boric acid, sodium borate, silica gel, arsenic compounds, and the like.

The insect growth regulators which may be incorporated into the carrier of the present invention include methoprene, Isopropyl (E,E)-11-methoxy-3,7,11-trimethyl-2,4-dodecadienoate and hydroprene ethyl (E,E)-3,7,11-trimethyl-2,4-dodecadienoate. By the use of insect growth regulators, it may prove possible to interrupt the life cycle of the insects, thereby controlling the colony. Thus, the use of this type of toxicant would have its desired effect in a long term fashion whereby the colony, unable to propagate, would decline in population.

The only restriction to be placed on the toxicants used in the present invention is that they should not be repellent to the insect to be controlled. Thus, pyrethroids are not expected to perform well due to their repellency action.

A method for control of pestiferous wasp colonies of the family Vespidae uses sex pheromones of female *Musca domestica* as kairomones. This method comprises concentrating the pheromones in an amount sufficient to attract pestiferous wasps in close proximity to a means to destroy the wasps. Another method for control of pestiferous wasp colonies of the family Vespidae, which method uses sex pheromones of female *Musca domestica* as wasp attractant kairomones, comprises interspersing saturated or unsaturated hydrocarbons having a carbon content of about $C_5$ to $C_{33}$, in an amount sufficient to attract wasps, among a powdered nonrepellent toxicant having delayed toxicity, the hydrocarbons acting as kairomones relative to the pestiferous wasps.

Finally, the attractant can be used in a trap whereby the kairomone is placed within a trap so the insects may enter the trap and are unable to escape. Thus, the trap would fill up with insects which would die of dessication or starvation after a few days thereby weakening the foraging ability of the colony and establishing a degree of control over those colonies.

The following examples are offered to illustrate the effectiveness of the present invention, and are not to be construed as limiting the scope or spirit of the invention.

In each of the examples I and II, treated pieces of filter paper (1 cm×2 cm) were placed in bottles in a yellowjacket cage and compared with bottles with filter paper but no treatment. There was an average of 0.41 wasps/minute (standard error=0.10) entering bottles with the untreated filter paper as compared to 1.26 wasps/minute (standard error=0.32) entering bottles with 5 microliters of (Z)-9-tricosene. This data is from 10 tests total including 2 nests of *Vespula germanica*, and 1 nest each of *Vespula flavopilosa* and *Vespula maculifrons*. The differences are highly significant by the paired t-test (P=0.002, where anything lower than 0.05 is considered significant).

EXAMPLE I

The data for saturated hydrocarbons are shown in the graph of FIG. 1. Y axis shows the number of entries per minute. The values for $C_{13}$, $C_{16}$ and $C_{23}$ are significantly greater than those of the blank (Dunnett's multiple range test in one-way analysis of variance, P is less than 0.05).

EXAMPLE II (Z)-9-heneicosene was tested against decane $C_{10}$ which possesses essentially the same activity as the blank. In this case, the number of wasps in the bottle was counted instantaneously at selected time intervals. Filter papers treated with decane had 0.56 wasps at any one time (standard error=0.25, N=18) vs 1.33 wasps (standard error=0.27) in bottles with filter papers treated with (Z)-9-heneicosene. These differences are significant by the chi-square test (P=0.016).

EXAMPLE III (Z)-9-tricosene was tested in the field by diluting the tricosene 1:1 with octane and adding 4 drops each to paper wrapped around 20 containers of 60 ml volume. 10 additional, similar containers without tricosene were also prepared. 10 locations were chosen at random. At each location, one treated container and one untreated container were placed 8 meters apart. The containers were checked at regular intervals and the number and species of insects on each container were recorded. On the average, 0.54 containers without tricosene were found per hour by *Vespula germanica*. 1.62 containers with tricosene were found per hour. The number of individuals on a container without tricosene increased at the rate of 0.13 individuals per container per hour. The rate of increase on containers with tricosene was 0.41 individuals per container per hour.

Other modifications of the invention will be apparent to those skilled in the art in light of the foregoing description without departing from the scope or spirit of the present invention. All alternative modifications and variations of the present invention which would follow in the spirit and broad scope of the appended claims are included.

We claim:

1. A method for controlling the population of wasps at a preselected area, the method comprising: applying to the preselected area a composition comprising a carrier matrix base, a wasp toxicant, and an effective amount of a compound that is a wasp-attracting housefly sex pheromone or a wasp-attracting homolog thereof, for controlling the wasps at the preselected area.

2. The method in accordance with claim 1 wherein the compound is selected from the group consisting of (Z)-9-tricosene, (Z)-9-heneicosene, tricosane, tridecane, and mixtures thereof.

3. The method in accordance with claim 1 wherein the wasp toxicant has delayed toxicity.

4. The method in accordance with claim 1 wherein the wasp-attracting housefly sex pheromone or homolog thereof is an aliphatic hydrocarbon compound having a carbon content of $C_5$ to $C_{33}$.

5. The method in accordance with claim 1 wherein the wasp-attracting housefly sex pheromone or homolog thereof is an aliphatic hydrocarbon compound having a carbon content of $C_8$ to $C_{23}$.

* * * * *